United States Patent
Guo

(10) Patent No.: US 9,548,147 B2
(45) Date of Patent: Jan. 17, 2017

(54) METAL OR METAL OXIDE COMPRISING A SURFACE-BONDED ORGANIC SHELL, AND A METHOD FOR PREPARING THE SAME

(71) Applicant: Beijing Gignano Biointerface Co. Ltd, Beijing (CN)

(72) Inventor: Boliang Guo, Wuxi (CN)

(73) Assignee: Beijing Gignano Biointerface Co. Ltd., Beijing (CN)

( * ) Notice: Subject to any disclaimer, the term of this patent is extended or adjusted under 35 U.S.C. 154(b) by 123 days.

(21) Appl. No.: 14/155,352

(22) Filed: Jan. 14, 2014

(65) Prior Publication Data

US 2014/0124696 A1    May 8, 2014

Related U.S. Application Data

(63) Continuation-in-part of application No. PCT/CN2012/078462, filed on Jul. 11, 2012.

(30) Foreign Application Priority Data

Jul. 15, 2011  (CN) .......................... 2011 1 0197600
Oct. 11, 2011  (CN) .......................... 2011 1 0305517

(51) Int. Cl.
| | | |
|---|---|---|
| *H01F 1/01* | (2006.01) | |
| *H01F 1/34* | (2006.01) | |
| *B22F 1/00* | (2006.01) | |
| *C09C 1/36* | (2006.01) | |
| *C09C 1/04* | (2006.01) | |
| *C09C 1/22* | (2006.01) | |
| *C09C 1/24* | (2006.01) | |
| *C09C 1/34* | (2006.01) | |
| *C01B 13/14* | (2006.01) | |
| *B82Y 30/00* | (2011.01) | |
| *A61K 49/18* | (2006.01) | |
| *G01N 33/543* | (2006.01) | |
| *H01F 1/00* | (2006.01) | |
| *B82Y 5/00* | (2011.01) | |

(52) U.S. Cl.
CPC ............. *H01F 1/01* (2013.01); *A61K 49/1833* (2013.01); *A61K 49/1857* (2013.01); *B22F 1/0062* (2013.01); *B82Y 30/00* (2013.01); *C01B 13/145* (2013.01); *C09C 1/043* (2013.01); *C09C 1/22* (2013.01); *C09C 1/24* (2013.01); *C09C 1/346* (2013.01); *C09C 1/3669* (2013.01); *G01N 33/5434* (2013.01); *H01F 1/342* (2013.01); *B82Y 5/00* (2013.01); *C01P 2004/62* (2013.01); *C01P 2004/64* (2013.01); *C01P 2004/80* (2013.01); *C01P 2006/42* (2013.01); *H01F 1/0054* (2013.01)

(58) Field of Classification Search
CPC ............... H01F 1/06; H01F 1/112; H01F 1/20
See application file for complete search history.

(56) References Cited

U.S. PATENT DOCUMENTS

| | | | | |
|---|---|---|---|---|
| 3,514,304 A * | 5/1970 | Binnis | ................... | C09C 1/3692 106/14.12 |
| 4,065,519 A * | 12/1977 | Koch | ................... | B29C 45/0001 264/122 |
| 6,794,265 B2 * | 9/2004 | Lee | ........................ | B82Y 10/00 252/301.6 F |
| 7,541,017 B2 * | 6/2009 | Bringley | .............. | B01J 13/0008 424/1.29 |
| 2005/0261479 A1 * | 11/2005 | Hoffmann | ........ | C07K 14/43518 530/353 |
| 2007/0003463 A1 * | 1/2007 | Ajiri | ........................ | B01J 3/006 423/274 |
| 2007/0004839 A1 * | 1/2007 | Yamamoto | ............... | C08K 3/08 524/417 |
| 2008/0203351 A1 * | 8/2008 | Gao | ..................... | A61K 49/186 252/62.51 R |
| 2009/0169478 A1 * | 7/2009 | Leuschner | ......... | A61K 49/1866 424/9.3 |
| 2009/0299127 A1 * | 12/2009 | Rudolph | .............. | A61K 9/0009 514/1.1 |

* cited by examiner

*Primary Examiner* — Carol M Koslow
(74) *Attorney, Agent, or Firm* — Matthias Scholl, PC; Matthias Scholl

(57) ABSTRACT

An organically surface-bonded metal or metal oxide material including an inorganic metal or metal oxide and an organic material. The organic material is coated on the surface of the inorganic metal or metal oxide. The inorganic metal or metal oxide and the organic material are linked through a strong chemical bond. The strong chemical bond includes a covalent bond between a metal in the inorganic metal or metal oxide and a nitrogen in the organic material.

3 Claims, No Drawings

METAL OR METAL OXIDE COMPRISING A SURFACE-BONDED ORGANIC SHELL, AND A METHOD FOR PREPARING THE SAME

CROSS-REFERENCE TO RELATED APPLICATIONS

This application is a continuation-in-part of International Patent Application No. PCT/CN2012/078462 with an international filing date of Jul. 11, 2012, designating the United States, and further claims priority benefits to Chinese Patent Application No. 201110197600.8 filed Jul. 15, 2011, and to Chinese Patent Application No. 201110305517.8 filed Oct. 11, 2011. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 14781 Memorial Drive, Suite 1319, Houston, Tex. 77079.

BACKGROUND OF THE INVENTION

Field of the Invention

The invention relates to a magnetic particle and an organically surface-bonded metal or metal oxide material, and a method for preparing the same.

Description of the Related Art

Organic-inorganic composites can present novel high-performance properties, the key to producing which is resolving organic-inorganic interface linkage. Conventional approaches mostly rely on physical interface methods, such as various spraying or coating techniques. The physical coating is not stable, and easy to fall off. Some chemical coating methods are also used to resolve organic-inorganic interface problems, such as surfactant coating, silane coupling agent method and so on. Most of the interfaces are formed through weak chemical interaction, such as coordination bond, hydrogen bond, electrostatic interaction and van der Waals interaction, which raise serious questions concerning the long-term stability. Therefore, a strong and stable bonding at the organic-inorganic interface remains a challenge to science and technology.

Functionalized magnetic particles can be accurately positioned, moved, controlled and separated under the control of applied magnetic field due to their special magnetic effect. As a kind of magnetic carrier or magnetic marker, functionalized magnetic nanoparticles can carry various drugs, or couple various biological ligands, thus form a variety of biological magnetic assembly system. They find a wide range of application in biological research, medical diagnosis and treatment, drug screening, biochemical products separation, food and environmental microbiological testing, and many other areas. Meanwhile, functionalized magnetic particles, especially those having nano-size have large specific surface area. They also have potential application in the field of chemical catalysis, environmental wastewater treatment, heavy metal recycling and etc.

There are many methods to synthesize magnetic particles, these inorganic magnetic particles have no functional groups on the surface, and thus it limits their practical application. Resent approaches are forming magnetic particle-organic material composites, including forming core-shell structure with organic material, such as surfactant coating, silanization method and etc., and forming magnetic polymer particles with polymers, such as blending embedding method, interface deposition method, monomer polymerization method and etc. However, the above methods have shortcomings and deficiencies of one kind or another. New method remains to be explored in order to produce functionalized magnetic particles with controllable size, narrow particle size distribution, strong magnetism, and high content of surface functional groups, as well as simple synthesis process.

SUMMARY OF THE INVENTION

In view of the above-described problems, it is one objective of the invention to provide an organically surface-bonded metal or metal oxide material, and a method of preparing the same. The organically surface-bonded metal or metal oxide material is provided with a strong covalent chemical bonding between the metal or metal oxide and an organic material.

It is another objective of the invention to provide an organically functionalized magnetic particle with controllable size, narrow particle size distribution, high specific saturation magnetization, and high content of surface functional groups, as well as a method of synthesizing the same.

To achieve the above objective, in accordance with one embodiment of the invention, there is provided an organically surface-bonded metal or metal oxide material comprising an inorganic metal or metal oxide and an organic material, the organic material coating on a surface of the inorganic metal or metal oxide. The inorganic metal or metal oxide and the organic material are linked through a strong chemical bond, and the strong chemical bond comprises a covalent bond between a metal in the inorganic metal or metal oxide and a nitrogen in the organic material.

In a class of this embodiment, the inorganic metal or metal oxide is a pure metal, or metal alloy, or metal oxide, or oxidized metal alloy, and the metal is selected from the group consisting of Fe, Ti, Cr, V, Mn, W, Co, Ni, Zn, Zr, Mg, Al, and Si.

In a class of this embodiment, the organic material coating on the surface of the inorganic metal or metal oxide is an organic compound comprising an amine group or a derivative thereof, comprising aliphatic amines, alcohol amines, amides, alicyclic amines, aromatic amines, naphthylamine and derivatives thereof; or the organic material is an organic polymer comprising an amine group or a derivative thereof, comprising a variety of synthetic or natural polymers with an amine functional group and derivatives thereof, such as polyethyleneimine (PEI) and the like; or the organic material is a mixture of the organic compound comprising the amine group and the organic polymer comprising the amine group.

According to the present invention, a method for preparation of the organically surface-bonded metal or metal oxide material comprises the steps of:

a) dispersing the inorganic metal or metal oxide in an organic phase comprising at least one organic compound with an amine group, and/or at least one organic polymer with an amine group; and b) reacting the inorganic metal or metal oxide with the amine groups in the organic phase at a temperature in the range of 50-300 degree Celsius.

In a class of this embodiment, the inorganic metal or metal oxide is a pure metal, or metal alloy, or metal oxide, or oxidized metal alloy, and the metal is selected from the group consisting of Fe, Ti, Cr, V, Mn, W, Co, Ni, Zn, Zr, Mg, Al, and Si.

In a class of this embodiment, the organic compound with the amine group is selected from aliphatic amines (such as ethylenediamine, hexamethylenediamine and other diamines), alcohol amines, amides, alicyclic amines, aromatic amines, naphthylamine and derivatives thereof; and the organic polymer with the amine group is selected from a variety of synthetic or natural polymers containing amine functional group and derivatives thereof, such as polyethyleneimine (PEI) and the like.

In a class of this embodiment, the organic phase is a liquid organic compound with an amine group; or the organic phase is a mixed solution of the organic compound with the amine group and an organic solvent; or the organic phase is a mixed solution of the organic polymer with the amine group and the organic solvent; or the organic phase is a mixed solution of the organic polymer with the amine group and the organic compound with the amine group; or the organic phase is a mixed solution of the organic polymer with the amine group, the organic compound with the amine group, and the organic solvent.

Compared with the traditional approaches on chemical modification of a metal or metal oxide material, the present invention provides a simple and effective method of coating an organic material on the surface of the metal or metal oxide through a direct one-step chemical reaction. It achieves the direct bonding between the organic material and the metal or metal oxide. The problem of inorganic-organic interface is solved perfectly with this method. The method is not only simple and easy to produce organically surface-bonded metal or metal oxide in large industrial scale, but also produced organically surface-bonded metal or metal oxide material has excellent properties. The advantages of the method are specifically reflected in the following areas:

1. The method is applicable for metal or metal oxide of various shape and size. For example, the metal or metal oxide with granular, acicular, flaky, blocky shape, or special-shaped device manufactured by various techniques can be surface modified with organic material by this method.

2. High content of organic functional group can be obtained on the surface of the metal or metal oxide by this method, and the functional group can be further modified by chemical or biological molecules.

3. The binding of the organic material coating with the inorganic metal or metal oxide is strong, it has a long-term chemical and physical stability and the organic material will not fall off the inorganic metal or metal oxide in the process of multi-reuse and further chemical reaction in different kind of reaction mediums and under various reaction conditions.

Properties of the above organically surface-bonded metal or metal oxide material meet the demand of application in the field of biology, medicine, pharmacy, energy, chemical engineering, environment and etc.

In another aspect, the invention provides a magnetic particle comprising a core and a shell, the core comprising an inorganic magnetic particle, the shell comprising an organic material, the organic material coating on a surface of the inorganic magnetic particle, the inorganic magnetic particle and the organic material being linked through a strong chemical bond to form a core-shell structure, wherein the core comprising the inorganic magnetic particle has a diameter in the range of from 2 nm to 20 μm, and the strong chemical bond comprises a covalent bond between a metal in the inorganic magnetic particle and a nitrogen in the organic material.

In a class of this embodiment, the inorganic magnetic particle is a ferrite having a general chemical formula of $XFe_2O_4$, where X represents a divalent iron ion ($Fe^{2+}$), or represents a divalent metal ion selected from the group consisting of $Mn^{2+}$, $Zn^{2+}$, $Cu^{2+}$, $Ni^{2+}$, $Mg^{2+}$, an $Co^{2+}$, or represents a divalent metal ion mixture comprising Ni—Zn and Mn—Mg—Zn; or the inorganic magnetic particle is an iron oxide; or the inorganic magnetic particle is a metallic iron; or the inorganic magnetic particle is an iron nitride; or the inorganic magnetic particle is a mixture of the ferrite, iron oxide, metallic iron, and iron nitride.

In a class of this embodiment, the organic material coating on the surface of the inorganic magnetic particle is an organic compound comprising an amine group or a derivative thereof, comprising aliphatic amines, alcohol amines, amides, alicyclic amines, aromatic amines, naphthylamine and derivatives thereof; or the organic material is an organic polymer comprising an amine group or a derivative thereof, comprising a variety of synthetic or natural polymers with an amine functional group and derivatives thereof, such as polyethyleneimine (PEI); or the organic material is a mixture of the organic compound comprising the amine group and the organic polymer comprising the amine group.

According to the present invention, a method for preparation of the magnetic particle comprises the steps of:
 a) dispersing the inorganic magnetic particle in an organic phase comprising at least one organic compound with an amine group, and/or at least one organic polymer with an amine group;
 b) reacting the inorganic magnetic particle with the amine groups in the organic phase at a temperature in the range of 50-300 degree Celsius.

In a class of this embodiment, the inorganic magnetic particle is a ferrite having a general chemical formula of $XFe_2O_4$, where X represents a divalent iron ion ($Fe^{2+}$), or represents a divalent metal ion selected from the group consisting of $Mn^{2+}$, $Zn^{2+}$, $Cu^{2+}$, $Ni^{2+}$, $Mg^{2+}$, and $Co^{2+}$, or represents a divalent metal ion mixture comprising Ni—Zn, Mn—Mg—Zn; or the inorganic magnetic particle is an iron oxide; or the inorganic magnetic particle is a metallic iron; or the inorganic magnetic particle is an iron nitride; or the inorganic magnetic particle is a mixture of the ferrite, iron oxide, metallic iron, and iron nitride; the inorganic magnetic particle core has a diameter in the range of from 2 nm to 20 μm, In a class of this embodiment, the organic compounds with the amine group is selected from aliphatic amines (such as ethylenediamine, hexamethylenediamine and other diamines), alcohol amines, amides, alicyclic amines, aromatic amines, naphthylamine and derivatives thereof.

In a class of this embodiment, the organic polymer with amine groups is selected from a variety of synthetic or natural polymers containing amine functional group and derivatives thereof, such as polyethyleneimine (PEI) and the like.

In a class of this embodiment, the organic phase is a liquid organic compound with an amine group; or the organic phase is a mixed solution of the organic compound with the amine group and an organic solvent; or the organic phase is a mixed solution of the organic polymer with the amine group and the organic solvent; or the organic phase is a mixed solution of the organic polymer with the amine group and the organic compound with the amine group; or the organic phase is a mixed solution of the organic polymer with the amine group, the organic compound with the amine group, and the organic solvent.

Compared with the conventional functionalized magnetic particles and the traditional approaches of synthesizing the same, the invention provides a simple and effective method of coating organic material on the surface of magnetic particle through a direct one-step chemical reaction. It achieves the direct bonding between organic material shell and inorganic magnetic particle core. The problem of interface between inorganic magnetic iron oxide particle and organic material is solved perfectly with this method. The method is not only simple and easy to produce functionalized magnetic particle in large industrial scale, but also produced functionalized magnetic particle has excellent properties. The advantages of the method are specifically reflected in the following areas:

1. The method is applicable for magnetic particles with various size and size distribution. Inorganic magnetic particles produced by various methods or commercial inorganic magnetic particles (comprising ferrite particles, ferric oxide, metal iron particles, iron nitride particles, etc.) can be surface-modified by this method.

2. The functionalized magnetic particle has high specific saturation magnetization and uniform magnetism. Because the organic material comprises a small mass ratio of the whole functionalized magnetic particle, the high specific saturation magnetization of functionalized magnetic particle close to the maximum value of inorganic magnetic particle, thus it is easy to separate and control magnetically.

3. The functionalized magnetic particle has high content of organic functional group, it achieves those of ion exchange resin, and the functional group can be further modified by chemical or biological molecules.

4. The binding of the organic material shell with the inorganic magnetic particle core is strong, it has a long-term chemical and physical stability and the organic material shell will not fall off the inorganic magnetic particle core in the process of multi-reuse and further chemical reaction in different kind of reaction mediums and under various reaction conditions.

5. Ethanediamine-functionalized magnetic particle is more hydrophilic, and has low nonspecific binding to biomolecules.

6. The functionalized magnetic particles are easy to disperse in solutions, easy to magnetically separate, redisperse and reuse.

As a kind of magnetic separation carrier or magnetic marker, properties of the above functionalized magnetic particle meet the demand of application in the field of biology, medicine, pharmacy, energy, chemical engineering, environment and the like.

DETAILED DESCRIPTION OF THE INVENTION

For further illustrating the invention, experiments detailing an organically surface-bonded metal or metal oxide material and a preparation method thereof are described below. It should be noted that the following examples are intended to describe and not to limit the invention.

Example 1

100 g of titanium oxide nanoparticles with an average size of 50 nm and 500 mL of ethylenediamine were added to a 1 liter of three-neck round-bottom flask equipped with a reflux condenser and a mechanical stirrer. The reaction system was heated to 120 degree Celsius and maintained at this temperature for 4 hrs with continuously being stirred. At the end of reaction, the ethylenediamine surface-bonded titanium oxide nanoparticles are collected by centrifuge, and followed by 3 times ultrasonic washing in ordinary water for 15 minutes each time.

The above ethylenediamine surface-bonded titanium oxide nanoparticles have core-shell structure, a titanium oxide core with an average size of 50 nm, and an ethylenediamine mono-molecular shell. The core and shell are linked through strong chemical bonds.

Example 2

500 g of zinc oxide nanoparticles with an average size 100 nm and 1000 mL of hexamethylenediamine were added to a 2 liter of three-neck round-bottom flask equipped with a reflux condenser and a mechanical stirrer. The reaction system was heated to 150 degree Celsius, and maintained at this temperature for 6 hrs with continuously being stirred. At the end of reaction, the hexamethylenediamine surface-bonded zinc oxide nanoparticles are collected by centrifuge, and followed by at least 3 times ultrasonic washing in ordinary water for 15 minutes each time.

The above hexamethylenediamine surface-bonded zinc oxide nanoparticles have core-shell structure, a zinc oxide core with an average size of 100 nm, and a hexamethylenediamine mono-molecular shell. The core and shell are linked through strong chemical bonds.

Example 3

100 g of chromic oxide particles with an average size of 200 nm and 500 mL of p-phenylenediamine were added to a 1 liter of three-neck round-bottom flask equipped with a reflux condenser and a mechanical stirrer. The reaction system was heated to 200 degree Celsius, and maintained at this temperature for 8 h with continuously being stirred. At the end of reaction, the p-phenylenediamine surface-bonded chromic oxide particles are collected by centrifuge, and followed by at least 5 times ultrasonic washing in ordinary water for 15 minutes each time.

The above p-phenylenediamine surface-bonded chromic oxide particles have core-shell structure, a chromic oxide core with an average size 200 nm, and a p-phenylenediamine mono-molecular shell. The core and shell are linked through strong chemical bonds.

Example 4

100 slice of titanium alloy (Ti6Al4V) with a size of 20 mm×20 mm×1 mm and 1000 mL of monoethanolamine were added to a 2 liter of three-neck round-bottom flask equipped with a reflux condenser and a mechanical stirrer. The reaction system was heated to 150 degree Celsius, and maintained at this temperature for 12 hrs with continuously being stirred. At the end of reaction, the monoethanolamine surface-bonded titanium alloy (Ti6Al4V) slice are collected by centrifuge, and followed by at least 3 times ultrasonic washing in ordinary water for 15 minutes each time.

The above monoethanolamine surface-bonded titanium alloy (Ti6Al4V) slice consist of a titanium alloy (Ti6Al4V) slice with a size of 20 mm×20 mm×1 mm and a monoethanolamine mono-molecular coating. The slice and coating are linked through strong chemical bonds.

Example 5

A solution of 250 mL of naphthalene diamine in 250 mL of dimethylformamide, and 100 g of stainless steel rod (316 L) with a diameter of 1 mm and a length of 10 mm were added to a 1 liter of three-neck round-bottom flask equipped with a reflux condenser and a mechanical stirrer. The reaction system was heated to 180 degree Celsius, and maintained at this temperature for 20 hrs with continuously being stirred. At the end of reaction, the naphthalene diamine surface-bonded stainless steel rod (316 L) are collected by centrifuge, and followed by at least 3 times ultrasonic washing in ethyl alcohol for 15 minutes each time.

The above naphthalene diamine surface-bonded stainless steel rod (316 L) comprises a stainless steel rod (316 L) and a naphthalene diamine mono-molecular coating, the rod and coating are linked through strong chemical bonds.

Example 6

A solution of 500 mL of polyethyleneimine in 500 mL of dimethyl sulfoxide, and 500 g of Co—Cr alloy wire network with a diameter of 1 mm and area of 10 mm×20 mm were added to a 2 liter of three-neck round-bottom flask equipped with a reflux condenser and a mechanical stirrer. The reaction system was heated to 200 degree Celsius, and maintained at this temperature for 15 hrs with continuously being stirred. At the end of reaction, the polyethyleneimine surface-bonded Co—Cr alloy wire network are collected by centrifuge, and followed by at least 3 times ultrasonic washing in ordinary water for 15 minutes each time.

The above polyethyleneimine surface-bonded Co—Cr alloy wire network comprises a Co—Cr alloy wire network and a polyethyleneimine mono-molecular coating, the wire network and coating are linked through strong chemical bonds.

Example 7

100 g of nitinol metal plate with a size of 20 mm×10 mm×3 mm and 500 g of octadecylamine were added to a 1 liter of three-neck round-bottom flask equipped with a reflux condenser and a mechanical stirrer. The reaction system was heated to 250 degree Celsius, and maintained at this temperature for 12 hrs with continuously being stirred. At the end of reaction, the octadecylamine surface-bonded nitinol metal plate are collected by centrifuge, and followed by at least 3 times ultrasonic washing in ethyl alcohol for 15 minutes each time.

The above hydrophobic octadecylamine surface-bonded nitinol metal plate comprises a nitinol metal plate and a hydrophobic octadecylamine mono-molecular coating. The plate and coating are linked through strong chemical bonds.

Example 8

A solution of 250 mL of ethylenediamine and 250 mL of polyethyleneimine in 500 mL dimethyl sulfoxide, and 500 g of magnesium alloy strip (AE21) with a size of 10 mm×2 mm×2 mm were added to a 2 liter of three-neck round-bottom flask equipped with a reflux condenser and a mechanical stirrer. The reaction system was heated to 120 degree Celsius, and maintained at this temperature for 8 h with continuously being stirred. At the end of reaction, the ethylenediamine/polyethyleneimine surface-bonded magnesium alloy strip (AE21) are collected by centrifuge, and followed by at least 3 times ultrasonic washing in ordinary water for 15 minutes each time.

The above ethylenediamine/polyethyleneimine surface-bonded magnesium alloy strip (AE21) comprises a magnesium alloy strip (AE21) and an ethylenediamine/polyethyleneimine mono-molecular coating. The strip and coating are linked through strong chemical bonds.

Example 9

100 g of commercial magnetite nanoparticles with an average size of 20 nm and 500 mL of ethylenediamine were added to a 1 liter of three-neck round-bottom flask equipped with a reflux condenser and a mechanical stirrer. The reaction system was heated to 120 degree Celsius and maintained at this temperature for 10 hrs with continuously being stirred. At the end of reaction, the ethylenediamine functionalized magnetite nanoparticles are collected by magnetic separation, and followed by 3 times ultrasonic washing in ordinary water for 15 minutes each time.

The above ethylenediamine functionalized magnetite nanoparticles have core-shell structure, a magnetite core with an average size of 20 nm, and an ethylenediamine mono-molecular shell. The core and shell are linked through strong chemical bonds.

Example 10

500 g of commercial magnetite nanoparticles with an average size of 60 nm and 1000 mL of hexamethylendiamine were added to a 2 liter of three-neck round-bottom flask equipped with a reflux condenser and a mechanical stirrer. The reaction system was heated to 150 degree Celsius and maintained at this temperature for 12 hrs with continuously being stirred. At the end of reaction, the hexamethylendiamine functionalized magnetite nanoparticles are collected by magnetic separation, and followed by 3 times ultrasonic washing in ordinary water for 15 minutes each time.

The above hexamethylendiamine functionalized magnetite nanoparticles have core-shell structure, a magnetite core with an average size 60 nm, and a hexamethylendiamine mono-molecular shell. The core and shell are linked through strong chemical bonds.

Example 11

100 g of commercial magnetite nanoparticles with an average size of 100 nm and 500 g of p-phenylenediamine were added to a 1 liter of three-neck round-bottom flask equipped with a reflux condenser and a mechanical stirrer. The reaction system was heated to 200 degree Celsius and maintained at this temperature for 15 hrs with continuously being stirred. At the end of reaction, the p-phenylenediamine functionalized magnetite nanoparticles are collected by magnetic separation, and followed by 5 times ultrasonic washing in ethyl alcohol for 15 minutes each time.

The above p-phenylenediamine functionalized magnetite nanoparticles have core-shell structure, a magnetite core with an average size 100 nm, and a p-phenylenediamine mono-molecular shell. The core and shell are linked through strong chemical bonds.

Example 12

500 g of magnetic cobalt ferrite nanoparticles with an average size of 5 nm and 1000 mL of monoethanolamine were added to a 2 liter of three-neck round-bottom flask equipped with a reflux condenser and a mechanical stirrer. The reaction system was heated to 150 degree Celsius and maintained at this temperature for 12 hrs with continuously being stirred. At the end of reaction, the monoethanolamine functionalized cobalt ferrite nanoparticles are collected by magnetic separation, and followed by 3 times ultrasonic washing in ordinary water for 15 minutes each time.

The above monoethanolamine functionalized cobalt ferrite nanoparticles have core-shell structure, a cobalt ferrite core with an average size of 5 nm, and a monoethanolamine mono-molecular shell. The core and shell are linked through strong chemical bonds.

Example 13

A solution of 250 mL of naphthalene diamine in 250 mL of dimethylformamide, and 100 g of magnetic manganese zinc ferrite nanoparticles with an average size of 1 µm were added to a 1 liter of three-neck round-bottom flask equipped with a reflux condenser and a mechanical stirrer. The reaction system was heated to 180 degree Celsius and maintained at this temperature for 20 hrs with continuously being stirred. At the end of reaction, the naphthalene diamine functionalized manganese zinc ferrite nanoparticles are collected by magnetic separation, and followed by 3 times ultrasonic washing in ethyl alcohol for 15 minutes each time.

The above naphthalene diamine functionalized manganese zinc ferrite nanoparticles have core-shell structure, a manganese zinc ferrite core with an average size of 1 µm, and a naphthalene diamine mono-molecular shell. The core and shell are linked through strong chemical bonds.

Example 14

A solution of 500 mL of polyethyleneimine in 500 mL of dimethyl sulfoxide, and 500 g of magnetic iron oxide particles with an average size of 5 µm were added to a 2 liter of three-neck round-bottom flask equipped with a reflux condenser and a mechanical stirrer. The reaction system was heated to 200 degree Celsius and maintained at this temperature for 15 hrs with continuously being stirred. At the end of reaction, the polyethyleneimine functionalized magnetic iron oxide particles are collected by magnetic separation, and followed by 3 times ultrasonic washing in ordinary water for 15 minutes each time.

The above polyethyleneimine functionalized magnetic iron oxide particles have core-shell structure, a magnetic iron oxide core with an average size of 5 µm, and a polyethyleneimine mono-molecular shell. The core and shell are linked through strong chemical bonds.

Example 15

500 g of octadecylamine and 100 g of metallic iron particles with an average size 10 µm were added to a 1 liter of three-neck round-bottom flask equipped with a reflux condenser and a mechanical stirrer. The reaction system was heated to 250 degree Celsius and maintained at this temperature for 20 hrs with continuously being stirred. At the end of reaction, the octadecylamine functionalized metallic iron particles are collected by magnetic separation, and followed by 3 times ultrasonic washing in ethyl alcohol for 15 minutes each time.

The above hydrophobic octadecylamine functionalized metallic iron particles have core-shell structure, a metallic iron core with an average size of 10 µm, and a hydrophobic octadecylamine mono-molecular shell. The core and shell are linked through strong chemical bonds.

Example 16

500 g of iron nitride nanoparticles with an average size of 500 nm and 1000 mL of ethylenediamine were added to a 1 liter of three-neck round-bottom flask equipped with a reflux condenser and a mechanical stirrer. The reaction system was heated to 60 degree Celsius and maintained at this temperature for 20 hrs with continuously being stirred. At the end of reaction, the ethylenediamine surface-bonded iron nitride nanoparticles are collected by magnetic separation, and followed by 3 times ultrasonic washing in ordinary water for 15 minutes each time.

The above ethylenediamine functionalized iron nitride nanoparticles have core-shell structure, an iron nitride nanoparticles core with an average size of 500 nm, and an ethylenediamine mono-molecular shell. The core and shell are linked through strong chemical bonds.

Example 17

A solution of 250 mL of ethylenediamine and 250 mL of polyethyleneimine in 500 mL of dimethyl sulfoxide, 500 g of magnetite nanoparticles with an average size of 10 nm were added to a 2 liter of three-neck round-bottom flask equipped with a reflux condenser and a mechanical stirrer. The reaction system was heated to 120 degree Celsius and maintained at this temperature for 20 hrs with continuously being stirred. At the end of reaction, the ethylenediamine/polyethyleneimine functionalized magnetite nanoparticles are collected by magnetic separation, and followed by 3 times ultrasonic washing in ordinary water for 15 minutes each time.

The above ethylenediamine/polyethyleneimine functionalized magnetite nanoparticles have core-shell structure, a magnetite nanoparticles core with an average size of 10 nm, and an ethylenediamine/polyethyleneimine mono-molecular shell. The core and shell are linked through strong chemical bonds.

Example 18

500 g of magnetite nanoparticles with an average size of 200 nm and 1000 mL of ethylenediamine were added to a 2 liter of three-neck round-bottom flask equipped with a reflux condenser and a mechanical stirrer. The reaction system was heated to 150 degree Celsius and maintained at this temperature for 20 hrs with continuously being stirred. At the end of reaction, the ethylenediamine functionalized magnetite nanoparticles are collected by magnetic separation, and followed by 3 times ultrasonic washing in ordinary water for 15 minutes each time.

The above ethylenediamine functionalized magnetite nanoparticles have core-shell structure, a magnetite nanoparticles core with an average size of 200 nm, and an ethylenediamine mono-molecular shell. The core and shell are linked through strong chemical bonds.

Example 19

After thorough ultrasonic cleansing of the ethylenediamine functionalized magnetite nanoparticles in Example 9 and Example 18 at least 5 times with 20 min each time in ethanol and distilled water, respectively, HRTEM, ATR-FTIR and XPS were used to characterize the magnetite nanoparticles. The HRTEM images show that the magnetite particle has an about 1 nm in thicknesses of Fe—N bond reaction layer surrounding the magnetite crystalline core, and has an ethylenediamine bright edge around the magnetite nanoparticles. The ATR-FTIR Spectra show a distinctive absorption bands of ethylenediamine (N—H bending, C—N stretching, C—H stretching), and present a sharp band of the Fe—N stretching vibration around 630 cm−1. The XPS spectrum show that after reaction the atomic concentrations of element N increases to 6.6%, and the Fe 2p peaks shift to lower binding energy at 710.4 and 723.5 eV which indicates that the surface Fe—O has been reduced to Fe—N by ethylenediamine. The above experimental data demonstrate that the magnetite nanoparticles have been connected successfully with ethylenediamine, and the linkage between the magnetic particle core and the ethylenediamine shell is a strong Fe—N covalent bonding between iron in the magnetite nanoparticle core and a nitrogen in the ethylenediamine, rather than a weak chemical bonding.

No change was detected in ATR-FTIR spectrum when ethylenediamine functionalized magnetite nanoparticles were left for more than one year on the lab bench, and/or were processed by power ultrasonic wave for more than 90 minutes. Furthermore, the amine groups on the surface of magnetite nanoparticles provide a anchor for further organic chemical reaction, for example, the amine groups can be transferred to carboxyl groups by reacting with maleic anhydride in Dimethyl Formamide at 50 degree Celsius for 12 hours or by ultrasonic reacting with citric acid in ethanol at 60 degree Celsius for 3 hours, and the amine groups can also be transferred to iminodiacetic acid (IDA) groups by reacting with sodium chloroacetate aqueous solution in pH 11 at 80 degree Celsius for 8 hours or to epoxy groups by reacting with epichlorohydrin in acetone at 50 degree Celsius for 12 hours and the like, ATR-FTIR spectrum confirmed that the above-mentioned reaction process were successful. Besides, the antibody can also be immobilized on the amine-functionalized magnetite nanoparticles by reacting with glutaraldehyde or on carboxyl-functionalized magnetite nanoparticles by reacting with carbodiimide for biomedical applications. All above these experiment data demonstrate that the ethylenediamine functionalized magnetite nanoparticles have a long-term chemical and physical stability, and the ethylenediamine shell will not fall off the magnetite nanoparticles core in the process of multi-reuse and further chemical reaction in different kind of reaction mediums and under various reaction conditions.

Example 20

As described in Example 19, after thorough ultrasonic cleansing of the ethylenediamine surface-bonded titanium oxide nanoparticles in the example 1, HRTEM images, ATR-FTIR Spectra and XPS spectrum show that the experiment result of the ethylenediamine surface-bonded titanium oxide nanoparticles is similar as the ethylenediamine functionalized magnetite nanoparticles in Example 19. It reveals that the titanium oxide nanoparticles have been connected successfully with ethylenediamine through Ti—N covalent bond.

No change was detected in ATR-FTIR spectrum when ethylenediamine functionalized titanium oxide were left on the lab bench for more than one year, and/or were processed by power ultrasonic wave for more than 90 minutes. Furthermore, the amine groups on the surface of titanium oxide provide an anchor for further organic chemical reaction as described in the example 19, for example, the amine groups reacting with maleic anhydride in Dimethyl Formamide, with citric acid in ethanol, with sodium chloroacetate aqueous solution, with polyvinyl alcohol by epichlorohydrin, with the antibody by glutaraldehyde or carbodiimide and the like. ATR-FTIR spectrum confirmed that the above-mentioned reaction process is successful. All these above experiment data demonstrate that the ethylenediamine functionalized titanium oxide have a long-term chemical and physical stability, and the ethylenediamine shell will not fall off the titanium oxide core in the process of multi-reuse and further chemical reaction in different kind of reaction mediums and under various reaction conditions.

Example 21

After thorough ultrasonic cleansing of the monoethanolamine surface-bonded titanium alloy (Ti6Al4V) slice in Example 4 at least 5 times with 20 min each time in ethanol and distilled water, respectively, ATR-FTIR, XPS and Contact angle measurement were used to characterize the surface of titanium alloy slice. The ATR-FTIR Spectra show a distinctive absorption bands of ethanolamine (N—H bending, C—N stretching, C—H stretching). The XPS spectrum show that after reaction the atomic concentrations of element N increased to 2.1%, and the Ti2p peaks shift from 466.6 eV to lower binding energy at 460.8 eV which indicates that the surface Ti—O has been reduced to Ti—N by ethanolamine. The water contact angle measurement show that the contact angles on the surface of titanium alloy slice increases from 23 to 56 degree after reaction. The above experimental data demonstrate that the titanium alloy slice has been coated successfully with ethanolamine, and the linkage between the titanium alloy slice and the ethanolamine coating is a strong Ti—N covalent bonding between titanium in the titanium alloy slice and a nitrogen in the ethanolamine, rather than a weak chemical bonding.

No change was detected in ATR-FTIR and XPS spectrum when the monoethanolamine surface-bonded titanium alloy slice were left on the lab bench for more than one year and were processed by power ultrasonic wave for more than 90 minutes. Furthermore, the hydroxyl groups on the surface of the monoethanolamine surface-bonded titanium alloy slice provide a anchor for further organic chemical reaction, for example, the hydroxyl groups can be transferred to epoxy groups by reacting with epichlorohydrin in acetone at 50 degree Celsius for 12 hours, and then the epoxy groups can react with Polyvinyl Alcohol, polyethyleneimine, or PEO-PPO-PEO block copolymer aqueous solution in pH11 at 80 degree Celsius for 12 hours. ATR-FTIR spectra confirmed that the above-mentioned reaction process is successful. Besides, some drug can also be immobilized on the surface of the titanium alloy slice for bioimplant and drug stent. All above these experiment data demonstrate that the monoethanolamine surface-bonded titanium alloy slice has a long-term chemical and physical stability, and the ethanolamine coating will not fall off the surface of titanium alloy slice in the process of multi-reuse and further chemical reaction in different kind of reaction mediums and under various reaction conditions.

The invention claimed is:

1. A method for preparation of a magnetic particle, the method comprising the steps of: a) dispersing an inorganic magnetic particle in an organic phase comprising at least one non-polymeric organic compound with an amine group; and b) reacting the inorganic magnetic particle with the amine group in the organic phase at a temperature in the range of 50-300 degree Celsius.

2. The method of claim 1, wherein the inorganic magnetic particle is a ferrite having a general chemical formula of $XFe_2O_4$, X represents a divalent iron ion ($Fe^{2+}$), or represents a divalent metal ion selected from the group consisting of $Mn^{2+}$, $Zn^{2+}$, $Cu^{2+}$, $Ni^{2+}$, $Mg^{2+}$, and $Co^{2+}$, or represents a divalent metal ion mixture comprising Ni—Zn and Mn—Mg—Zn; or the inorganic magnetic particle is an iron oxide; or the inorganic magnetic particle is a mixture of the ferrite, iron oxide, metallic iron, and iron nitride.

3. The method of claim 1, wherein the organic compound is an aliphatic amine, an alkanolamine, an amide, an alicyclic amine, or an aromatic amine.

\* \* \* \* \*